United States Patent
Han et al.

(10) Patent No.: US 11,378,486 B2
(45) Date of Patent: Jul. 5, 2022

(54) POLLUTANT GENERATION SYSTEM AND MONITORING SYSTEM FOR WIND TUNNEL TESTS

(71) Applicant: CHANGSHA UNIVERSITY OF SCIENCE & TECHNOLOGY, Hunan (CN)

(72) Inventors: Yan Han, Hunan (CN); Lian Shen, Hunan (CN); Chunsheng Cai, Hunan (CN); Baoxi Xiao, Hunan (CN); Chunguang Li, Hunan (CN); Peng Hu, Hunan (CN); Kuo Wang, Hunan (CN)

(73) Assignee: CHANGSHA UNIVERSITY OF SCIENCE & TECHNOLOGY, Hunan (CN)

( * ) Notice: Subject to any disclaimer, the term of this patent is extended or adjusted under 35 U.S.C. 154(b) by 293 days.

(21) Appl. No.: 16/842,789

(22) Filed: Apr. 8, 2020

(65) Prior Publication Data
US 2020/0232953 A1    Jul. 23, 2020

Related U.S. Application Data

(63) Continuation-in-part of application No. PCT/CN2018/121653, filed on Dec. 18, 2018.

(30) Foreign Application Priority Data

Dec. 20, 2017  (CN) .......................... 201711385543.X

(51) Int. Cl.
*G01M 9/04* (2006.01)
*G01M 9/06* (2006.01)
(Continued)

(52) U.S. Cl.
CPC .............. *G01M 9/04* (2013.01); *G01M 9/062* (2013.01); *G01M 9/065* (2013.01); *G01N 30/38* (2013.01);
(Continued)

(58) Field of Classification Search
CPC ........ G01M 9/04; G01M 9/062; G01M 9/065; G01N 33/0004; G01N 33/0075
See application file for complete search history.

(56) References Cited

U.S. PATENT DOCUMENTS 5,119,669 A * 6/1992 Silvis ..................... G01N 30/12
73/23.35

FOREIGN PATENT DOCUMENTS

CN         1800820        7/2006
CN       101509826        8/2009
(Continued)

OTHER PUBLICATIONS

Sharma, N. et al. "Application of Wind Tunnel to Air Pollution Problems", Journal of the Institution of Engineers (India): Environmental Engineering Division. 80(2): 35-43. Feb. 2000. (Year: 2000).*

*Primary Examiner* — Paul M. West
(74) *Attorney, Agent, or Firm* — JCIP Global Inc.

(57) ABSTRACT

The present invention discloses a pollutant generation system. The pollutant generation system includes a pollution source and a pollutant emitter. The pollutant emitter is connected to the pollution source. The pollution source is composed of two gases including air and methane. The flows of the gases are strictly controlled. Then, the gases enter a magnetic bead glass bottle. Due to the disturbance of magnetic beads to the flowing of the gases, the gases are sufficiently disordered, and the two gases are sufficiently mixed by using a spiral tube to generate a uniform and stable pollution source.

15 Claims, 3 Drawing Sheets

(51) Int. Cl.
  *G01N 33/00* (2006.01)
  *G01N 30/38* (2006.01)
  *G01N 15/06* (2006.01)
  *G01N 15/00* (2006.01)

(52) U.S. Cl.
  CPC ..... *G01N 33/0004* (2013.01); *G01N 33/0075* (2013.01); *G01N 15/06* (2013.01); *G01N 2015/0046* (2013.01); *G01N 2015/0092* (2013.01)

(56) References Cited

FOREIGN PATENT DOCUMENTS

| | | |
|---|---|---|
| CN | 102580603 | 7/2012 |
| CN | 106840578 | 6/2017 |
| CN | 107398190 | 11/2017 |
| CN | 108106811 | 6/2018 |
| JP | H09264808 | 10/1997 |

\* cited by examiner

POLLUTANT GENERATION SYSTEM AND MONITORING SYSTEM FOR WIND TUNNEL TESTS

CROSS-REFERENCE TO RELATED APPLICATION

This application is a continuation in part of international PCT application serial no. PCT/CN2018/121653, filed on Dec. 18, 2018, which claims the priority benefit of China application no. 201711385543.X, filed on Dec. 20, 2017. The entirety of each of the above-mentioned patent applications is hereby incorporated by reference herein and made a part of this specification.

BACKGROUND

Technical Field

The present invention relates to the technical field of pollutant monitoring and in particular to a pollutant generation system and monitoring system for wind tunnel tests.

Description of Related Art

Nowadays air pollution is a major health hazard in the daily life of humans in the world. To cope with the air pollution problems, many research institutions have carried out wind tunnel tests to simulate the dispersion of pollutants. However, limited by equipment and process reasons, the simulation results are not satisfactory. Some institutions adopt PIV to simulate the dispersion of pollutants, which is not widely applicable due to high costs. Conventional pollutant generation systems are mostly qualitative in nature and can only predict the trend of distribution of pollutants, but provides no detailed data about the distribution of pollutants in the simulation area. Also, there are few pollutant source generation and monitoring systems.

Therefore, it is necessary to provide a pollutant generation system and monitoring system for wind tunnel tests to solve the defects in the prior art.

Technical Problem

To solve the problems in the prior art, an objective of the present invention is to provide a pollutant generation system and monitoring system for wind tunnel tests which can generate a stable pollution source composed of uniformly distribute gases and achieve the convenient and rapid monitoring of pollutants.

SUMMARY

In order to achieve the objective, the present invention provides the following solutions. The present invention provides a pollutant generation system for wind tunnel tests, including a pollution source and a pollutant emitter. The pollutant emitter is connected to the pollution source. The pollutant emitter is arranged in a simulation area in a wind tunnel. A magnetic bead glass bottle is further arranged between the pollutant emitter and the pollution source. One end of the magnetic bead glass bottle is connected to the pollutant emitter. The other end of the magnetic bead glass bottle is connected to the pollution source. A spiral tube is further arranged between the magnetic bead glass bottle and the pollutant emitter.

Preferably, the pollution source includes air and methane, the air is supplied by an air pump, the methane is supplied by a methane supply tank, and both the air pump and the methane supply tank are connected to the magnetic bead glass bottle by using pipelines.

Preferably, the magnetic bead glass bottle serves as a mixing device and is arranged before the pollutant emitter; and the pipelines for connecting the air pump and the methane supply tank to the magnetic bead glass bottle are provided with flowmeters, and a flowmeter is arranged between the magnetic bead glass bottle and the pollutant emitter.

The present invention further discloses a pollutant monitoring system for wind tunnel tests, including the pollutant generation system for wind tunnel tests. The pollutant monitoring system further includes a wind tunnel and a pollutant concentration monitoring system. The pollutant concentration monitoring system is arranged in the wind tunnel. The pollutant concentration monitoring system includes a monitoring tube, a collecting bag and a chromatographic analyzer. The monitoring tube is arranged in a simulation area in the wind tunnel. A tail end of the monitoring tube is connected to the collecting bag. The collecting bag is further connected to the chromatographic analyzer.

Preferably, a plurality of monitoring tubes are provided and are fixedly arranged on a fixed frame in the wind tunnel by a collecting rake.

Preferably, a delivery pump is arranged between the collecting bag and the monitoring tube, and polluted gases collected by the monitoring tube are pumped into the collecting bag by virtue of the delivery pump.

Preferably, the pollutant monitoring system further includes a computer, and the chromatographic analyzer is connected to the computer.

Beneficial Effects of the Invention

Beneficial Effects

Compared with the prior art, the present invention achieves the following technical effects:

1. With the configuration of the magnetic bead glass bottle, due to the disturbance of magnetic beads to gases, the gases are sufficiently disordered; and the spiral tube is arranged after the magnetic bead glass bottle so that the two gases are sufficiently mixed to generate a uniform and stable pollution source.

2. The gases in the wind tunnel are analyzed by using the chromatographic analyzer, so that the distribution of pollutant concentrations in the simulation area can be intuitively and visually obtained.

BRIEF DESCRIPTION OF THE DRAWINGS

To describe the technical solutions of the embodiments of the present invention or the prior art more clearly, the following briefly introduces the accompanying drawings required for describing the embodiments. Apparently, the accompanying drawings in the following description show only some embodiments of the present invention, and a person of ordinary skill in the art may still derive other drawings from these accompanying drawings without creative efforts.

DETAILED DESCRIPTION

The following clearly and completely describes the technical solutions in the embodiments of the present invention with reference to the accompanying drawings in the embodiments of the present invention. Obviously, the described embodiments are only some embodiments instead of all embodiments of the present invention. All other embodiments obtained by a person of ordinary skill in the art based on the embodiments of the present invention without creative effects shall fall within the protection scope of the present invention.

To solve the problems in the prior art, an objective of the present invention is to provide a pollutant generation system and monitoring system for wind tunnel tests which can generate a stable pollution source composed of uniformly distribute gases and achieve the convenient and rapid monitoring of pollutants.

To make the objectives, features, and advantages of the present invention more obvious and comprehensible, the present invention is further described in detail below with reference to the accompanying drawings and specific implementations.

Figure 1:
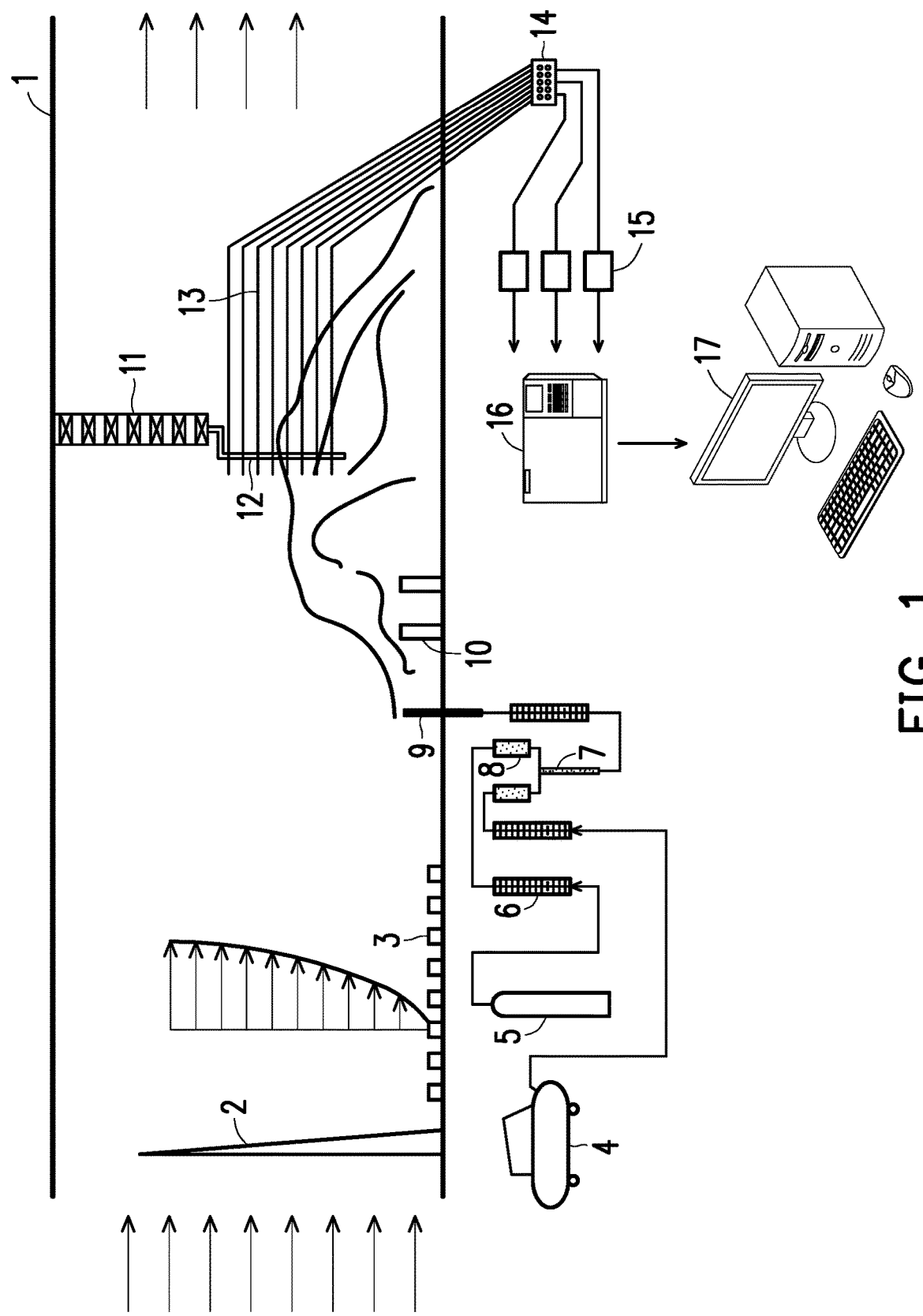
FIG. 1 illustrates a schematic structural diagram of a pollutant generation system and monitoring system for wind tunnel tests according to an embodiment of the invention.
Figure 2:
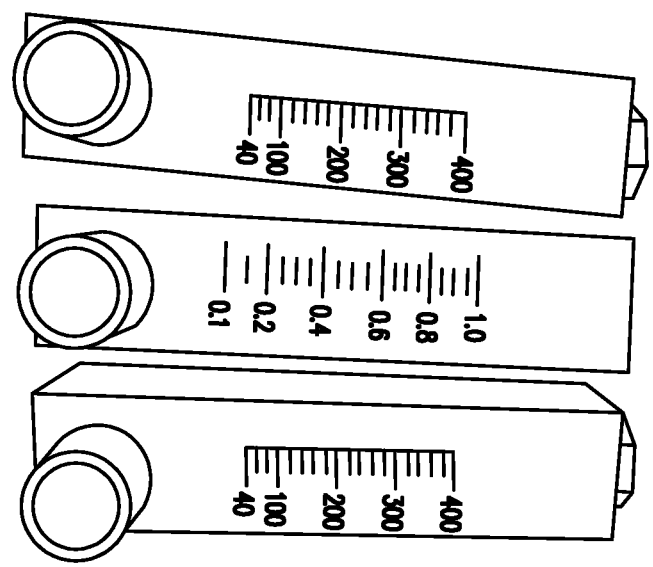
FIG. 2 illustrates a diagram of flowmeters according to an embodiment of the invention.
Figure 3:
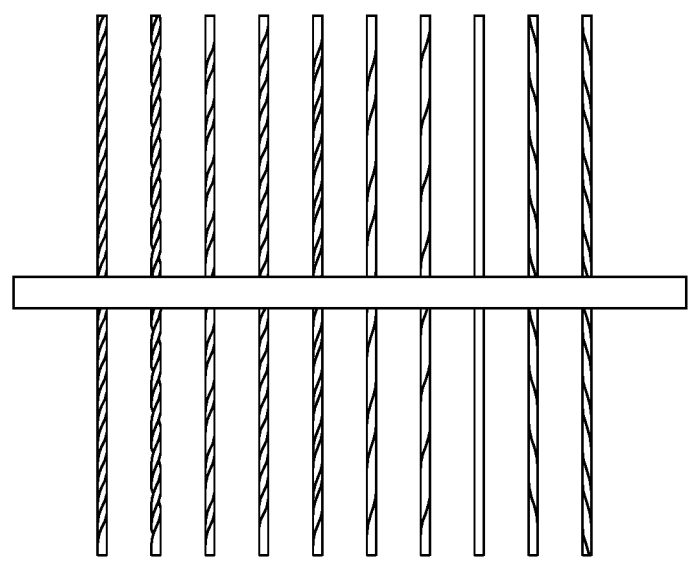
FIG. 3 illustrates a diagram of a collecting rake according to an embodiment of the invention.
Figure 4:
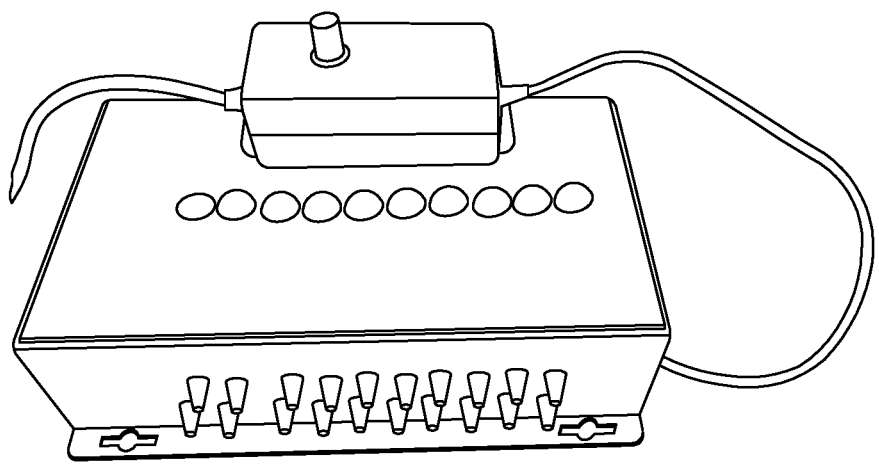
FIG. 4 illustrates a diagram of a delivery pump according to an embodiment of the invention.

The present invention provides a pollutant generation system for wind tunnel tests, as shown in FIG. 1, including a pollution source and a pollutant emitter 9. The pollutant emitter 9 is connected to the pollution source. The pollutant emitter 9 is placed in a simulation area in a wind tunnel 1 and is configured to emit pollutants. A magnetic bead glass bottle 8 is further arranged between the pollutant emitter 9 and the pollution source. One end of the magnetic bead glass bottle 8 is connected to the pollutant emitter 9. The other end of the magnetic bead glass bottle 8 is connected to the pollution source. A spiral tube 7 is further arranged between the magnetic bead glass bottle 8 and the pollutant emitter 9.

The pollution source includes air and methane. The air is supplied by an air pump 4, the methane is supplied by a methane supply tank 5, and both the air pump 4 and the methane supply tank 5 are connected to the magnetic bead glass bottle 8 by using pipelines. The pollution source in the present invention is a mixed gas of the air and the methane. The air and the methane are mixed after entering the magnetic bead glass bottle 8 through the pipelines. The air pump 4 supplies power for the mixed gas to cause the mixed gas to flow. The magnetic bead glass bottle 8 is an ordinary glass bottle filled with magnetic beads. Due to the disturbance of the magnetic beads to the gases, the gases are sufficiently disordered. An air pressure valve is mounted before the magnetic bead glass bottle 8 to control the speed at which the gases flow in or out of the glass bottle. The spiral tube 7 is further arranged between the magnetic bead glass bottle 8 and the pollutant emitter 9. The gases enter the spiral tube 7 after flowing out of the magnetic bead glass bottle 8. The spiral tube 7 is composed of a sealed glass tube to ensure that the two gases are sufficiently and uniformly mixed to form a uniform and stable pollution source.

The pipelines for connecting the air pump 4 and the methane supply tank 5 to the magnetic bead glass bottle 8 are provided with flowmeters 6 by which the flow velocities of the air and the methane are controlled. A flowmeter 6 is arranged between the magnetic bead glass bottle 8 and the pollutant emitter 9 to control the output flow velocity of the pollutants. Finally, a mixed gas pollutant composed of the air and the methane is released before a test area.

The present invention further discloses a pollutant monitoring system for wind tunnel tests, including the pollutant generation system for wind tunnel tests. The pollutant monitoring system further includes a wind tunnel 1 and a pollutant concentration monitoring system. The pollutant concentration monitoring system is arranged in the wind tunnel 1. The pollutant concentration monitoring system includes a monitoring tube 13, a collecting bag 15 and a chromatographic analyzer 16. The monitoring tube 13 is arranged in a simulation area in the wind tunnel 1. A tail end of the monitoring tube 13 is connected to the collecting bag 15. The collecting bag 15 is further connected to the chromatographic analyzer 16.

Polluted gases of the simulation area in the wind tunnel 1 are quantitatively collected by virtue of the monitoring tube 13. A plurality of monitoring tubes 13 are provided and are fixedly arranged on a fixed frame 11 by a collecting rake 12, and the fixed frame 11 is fixedly arranged in the wind tunnel 1. A delivery pump 14 is arranged between the tail ends of the plurality of the monitoring tubes 13 and the collecting bag 15, and the polluted gases collected by the monitoring tubes 13 are pumped into the collecting bag 15 by virtue of the delivery pump 14, so that the delivery efficiency is increased. A plurality of collecting bags 15 are provided. The collecting bags 15 are vacuum bags, so that the collecting bags 15 do not contain any residual gas which may affect the measurement of the concentrations of pollutants.

The collecting bags 15 are directly connected to the chromatographic analyzer 16. The polluted gases in the collecting bags 15 are chromatographically analyzed by the chromatographic analyzer 16, and then, the analysis result is uploaded to a computer 17 connected to the chromatographic analyzer 16, so that the distribution of a pollutant concentration in the simulation area can be intuitively and visually obtained.

The wind tunnel 1 is further provided with a wedge 2 and roughness elements 3. The wedge 2 and the roughness elements 3 are arranged at an entrance of the wind tunnel 1 and are used for simulating an entrance incoming flow of an atmospheric turbulent boundary layer. The test area of the wind tunnel 1 is further provided with building models 10.

The pollutant generation system and monitoring system for wind tunnel tests according to the present invention can generate a stable pollution source composed of uniformly distributed gases and achieve the convenient and rapid monitoring of pollutants.

Specific examples are used in the present invention to describe the principle and implementations of the present invention. The descriptions of the foregoing embodiments are merely intended to help understand the method and concept of the present invention. In addition, based on the concept of the present invention, a person of ordinary skill in the art may make modifications with respect to the specific implementations and the application scope. Therefore, the content of this specification shall not be construed as a limitation on the present invention.

What is claimed is:

1. A pollutant generation system for wind tunnel tests, comprising:
   a pollution source; and
   a pollutant emitter being connected to the pollution source;
   wherein the pollutant emitter is arranged in a simulation area in a wind tunnel, a magnetic bead glass bottle is further arranged between the pollutant emitter and the pollution source, one end of the magnetic bead glass bottle is connected to the pollutant emitter, another end of the magnetic bead glass bottle is connected to the pollution source, and a spiral tube is further arranged between the magnetic bead glass bottle and the pollutant emitter.

2. The pollutant generation system for wind tunnel tests according to claim 1, wherein the pollution source comprises air and methane, the air is supplied by an air pump, the methane is supplied by a methane supply tank, and both the air pump and the methane supply tank are connected to the magnetic bead glass bottle by pipelines.

3. The pollutant generation system for wind tunnel tests according to claim 2, wherein the pipelines for connecting the air pump and the methane supply tank to the magnetic bead glass bottle are provided with flowmeters, and each of the flowmeters is arranged between the magnetic bead glass bottle and the pollutant emitter.

4. A pollutant monitoring system for wind tunnel tests, comprising:
   the pollutant generation system for wind tunnel tests according to claim 3;
   a wind tunnel; and
   a pollutant concentration monitoring system being arranged in the wind tunnel, and the pollutant concentration monitoring system comprising:
      a plurality of monitoring tubes;
      a plurality of collecting bags; and
      a chromatographic analyzer;
   wherein the plurality of monitoring tubes are arranged in a simulation area in the wind tunnel, a tail end of each of the plurality of the monitoring tubes is connected to each of the plurality of collecting bags, and each of the plurality of collecting bags is further connected to the chromatographic analyzer.

5. The pollutant monitoring system for wind tunnel tests according to claim 4, wherein each of the plurality of monitoring tubes is fixed on a fixed frame in the wind tunnel by a collecting rake.

6. The pollutant monitoring system for wind tunnel tests according to claim 5, wherein the pollutant concentration monitoring system further comprising:
   a plurality of delivery pumps, each of the plurality of delivery pumps is arranged between the each of the plurality of collecting bags and the each of the plurality of monitoring tubes, and polluted gases collected by the plurality of monitoring tubes are pumped into the plurality of collecting bags by the delivery pump.

7. The pollutant monitoring system for wind tunnel tests according to claim 6, further comprising:
   a computer being connected to the chromatographic analyzer.

8. A pollutant monitoring system for wind tunnel tests, comprising:
   the pollutant generation system for wind tunnel tests according to claim 2;
   a wind tunnel; and
   a pollutant concentration monitoring system being arranged in the wind tunnel, and the pollutant concentration monitoring system comprising:
      a plurality of monitoring tubes;
      a plurality of collecting bags; and
      a chromatographic analyzer;
   wherein the plurality of monitoring tubes are arranged in a simulation area in the wind tunnel, a tail end of each of the plurality of the monitoring tubes is connected to each of the plurality of collecting bags, and each of the plurality of collecting bags is further connected to the chromatographic analyzer.

9. The pollutant monitoring system for wind tunnel tests according to claim 8, wherein each of the plurality of monitoring tubes is fixed on a fixed frame in the wind tunnel by a collecting rake.

10. The pollutant monitoring system for wind tunnel tests according to claim 9, wherein the pollutant concentration monitoring system further comprising:
    a plurality of delivery pumps, each of the plurality of delivery pumps is arranged between the each of the plurality of collecting bags and the each of the plurality of monitoring tubes, and polluted gases collected by the plurality of monitoring tubes are pumped into the plurality of collecting bags by the delivery pump.

11. The pollutant monitoring system for wind tunnel tests according to claim 10, further comprising:
    a computer being connected to the chromatographic analyzer.

12. A pollutant monitoring system for wind tunnel tests, comprising:
    the pollutant generation system for wind tunnel tests according to claim 1;
    a wind tunnel; and
    a pollutant concentration monitoring system being arranged in the wind tunnel, and the pollutant concentration monitoring system comprising:
       a plurality of monitoring tubes;
       a plurality of collecting bags; and
       a chromatographic analyzer;
    wherein the plurality of monitoring tubes are arranged in a simulation area in the wind tunnel, a tail end of each of the plurality of the monitoring tubes is connected to each of the plurality of collecting bags, and each of the plurality of collecting bags is further connected to the chromatographic analyzer.

13. The pollutant monitoring system for wind tunnel tests according to claim 12, wherein each of the plurality of monitoring tubes is fixed on a fixed frame in the wind tunnel by a collecting rake.

14. The pollutant monitoring system for wind tunnel tests according to claim 13, wherein the pollutant concentration monitoring system further comprising:
    a plurality of delivery pumps, each of the plurality of delivery pumps is arranged between the each of the plurality of collecting bags and the each of the plurality of monitoring tubes, and polluted gases collected by the plurality of monitoring tubes are pumped into the plurality of collecting bags by the delivery pump.

15. The pollutant monitoring system for wind tunnel tests according to claim 14, further comprising:
    a computer being connected to the chromatographic analyzer.

* * * * *